US008555698B2

(12) United States Patent
Neugebauer et al.

(10) Patent No.: US 8,555,698 B2
(45) Date of Patent: Oct. 15, 2013

(54) ENGINEERED SURFACES FOR LABORATORY TREAD WEAR TESTING OF TIRES

(75) Inventors: Paul M. Neugebauer, Akron, OH (US); Erik Knuth, Hudson, OH (US); David O. Stalnaker, Hartville, OH (US); Craig K. McClung, North Canton, OH (US); Alleva Lorenzo, Rome (IT); Kurata Takayuki, Kokubunji (JP); Yukitake Kosuke, Saitama (JP); Hiroshi Egami, Kodaira (JP); Alberto del Grosso, Kodaira (JP)

(73) Assignees: Bridgestone Americas Tire Operations, LLC, Nashville, TN (US); Bridgestone Corporation, Tokyo (JP)

( * ) Notice: Subject to any disclaimer, the term of this patent is extended or adjusted under 35 U.S.C. 154(b) by 365 days.

(21) Appl. No.: 13/013,870

(22) Filed: Jan. 26, 2011

(65) Prior Publication Data
US 2012/0186324 A1    Jul. 26, 2012

(51) Int. Cl.
*G01N 19/02* (2006.01)
(52) U.S. Cl.
USPC ..................................... 73/8; 73/146; 73/105
(58) Field of Classification Search
USPC ...................................................... 73/8, 146
See application file for complete search history.

(56) References Cited

U.S. PATENT DOCUMENTS

| | | | |
|---|---|---|---|
| 3,957,525 A | 5/1976 | Lees et al. | |
| 4,105,458 A | 8/1978 | Lees et al. | |
| RE30,047 E | 7/1979 | Lees et al. | |
| 4,588,443 A | 5/1986 | Bache | |
| 4,915,539 A | 4/1990 | Yoshikane et al. | |
| 5,352,062 A | 10/1994 | Yoshida et al. | |
| 5,376,700 A | 12/1994 | Yamazaki et al. | |
| 6,089,290 A | 7/2000 | Chlebina et al. | |
| 6,479,570 B2 | 11/2002 | Kamaishi et al. | |
| 6,532,811 B2 | 3/2003 | Turner et al. | |
| 6,804,998 B2 | 10/2004 | Turner et al. | |

(Continued)

FOREIGN PATENT DOCUMENTS

| | | | |
|---|---|---|---|
| JP | 06129954 A | * | 5/1994 |
| JP | 7020030 A | | 1/1995 |
| JP | 3234678 | | 9/2001 |

OTHER PUBLICATIONS

Walraven, "Laboratory Tread Wear Simulation," MTS Systems Corporation, Presented at a meeting of the Rubber Division, American Chemical Society, Cleveland, Ohio, 12 pages (Oct. 17-20, 1995).

(Continued)

*Primary Examiner* — Hezron E Williams
*Assistant Examiner* — Paul West

(57) ABSTRACT

A method of fabricating a substantially rigid hardened wear surface for a tire tread wear testing apparatus is provided, the method comprising making a cast of a road surface on which tread wear of the tire is to be tested, providing a layer of adhesive mixed with at least one aggregate and configured for hardening to create the substantially rigid hardened wear surface, while the layer of adhesive is unhardened: (a) coating the layer of adhesive onto a road wheel of the tire tread wear testing apparatus, and (b) stamping an impression of the cast into the layer of epoxy adhesive for producing the wear surface adapted for emulating one or more surface roughness characteristics of the road surface.

37 Claims, 15 Drawing Sheets

(56) References Cited

U.S. PATENT DOCUMENTS

| | | |
|---|---|---|
| 7,022,753 B2 | 4/2006 | Fogal, Sr. |
| 7,228,732 B2 | 6/2007 | Turner et al. |
| 7,254,996 B2 | 8/2007 | Ouyang |
| 7,312,262 B2 | 12/2007 | Donelson et al. |
| 7,384,469 B2 | 6/2008 | Matsuoka et al. |
| 7,448,261 B2 | 11/2008 | Ouyang |
| 7,680,610 B2 | 3/2010 | Miyashita et al. |
| 2002/0062907 A1 | 5/2002 | Jonsson et al. |
| 2003/0091815 A1 | 5/2003 | Buccellato et al. |
| 2003/0199626 A1 | 10/2003 | Lin et al. |
| 2004/0242432 A1 | 12/2004 | Suzuki et al. |
| 2007/0256484 A1 | 11/2007 | Imanishi et al. |
| 2009/0120178 A1 | 5/2009 | Iwase |
| 2009/0145214 A1* | 6/2009 | Muhlhoff et al. ............... 73/146 |
| 2009/0169901 A1 | 7/2009 | Blacklidge |

OTHER PUBLICATIONS

Parekh et al., "Evolution of Tire Wear Testing Technology," Tire Technology International, pp. 23-28 (1997).

Parekh et al., "Laboratory Tire Wear Simulation Process Using ADAMS Vehicle Model," SAE International, International Congress & Exposition, Detroit, Michigan, SAE Technical Paper Series 961001, 12 pages (Feb. 26-29, 1996).

Kim, Myoung Chan, International Search Report and Written Opinion, Aug. 24, 2012, pp. 1-11, Korean Intellectual Property Office.

* cited by examiner

ENGINEERED SURFACES FOR LABORATORY TREAD WEAR TESTING OF TIRES

FIELD OF THE INVENTION

This invention relates generally to the field of new and retread tire manufacture and design, including tread wear testing of tires and the fabrication of wear surfaces for such testing.

BACKGROUND OF THE INVENTION

In the laboratory, tire manufacturing and design may include evaluating tire tread wear performance with road wheel testing. Usually large diameter road wheels, such as 3 meters, are used to minimize the drum curvature effects on the tire's contact area and pressure distribution within the contact area. Many test machines can apply forces to the tire that are typical of actual vehicle loads—such as the radial, lateral, braking, and driving forces.

An abrasive surface may be provided over the outer surface of the road wheel. As the tire is rotated in contact with this surface, microscopic particles of tread rubber are worn off. The rate of wear and the uniformity of the wear over the tire surface are measured in order to assure acceptable tread wear performance of the tire in consumer service. Most common abrasive surfaces used in the tire industry for laboratory tread wear testing of tires are various grits of commercially available sand paper with adhesive backing, which are chosen for their high level of abrasiveness and ease of attachment to the road wheel with no consideration of roughness values or the structure of actual pavements. Prior techniques for matching roughness values from actual pavements relied on mixing hard aggregates, such as silica sand, with an epoxy resin bonding agent, such as in Japanese Patent Application Publication No. JP 07-020030 (A), filed Jun. 16, 1993, now Japanese Patent No. JP 3234678 (B2), which is assigned to the assignee of the present application. Another technique involved using cast polyurethane to create a flexible material with texture of asphalt or concrete and adding grit to increase abrasiveness, such as in Walraven, *Laboratory Tread Wear Simulation*, MTS Systems Corporation, Oct. 17-20, 1995. The resulting material was designed for a tread wear machine that employed a small radius flexible belt test surface that came in contact with a test tire. Thus, the resulting material also had to be flexible in order to accommodate for the flexibility of the belt and prevent cracking of the wear surface. However, such technique was inferior to using adhesive-backed sand paper and suffered from unacceptable problems such as short service expectancy due to the flexibility and softness of the resulting wear surface.

In a different field of noise testing, sound signatures of various tires have been measured by bringing the tire in contact with a road wheel coated with a wear surface made from a cast of a road. However, such wear surfaces did not contain any aggregate and were not optimized for emulating the surface roughness characteristics of a broad range of actual road surfaces. Furthermore, such wear surfaces were not selected to provide an extended service life since they were not used for testing tread wear.

BRIEF SUMMARY OF THE INVENTION

Embodiments of the invention are used for design and manufacturing of new and retreaded tires, including passenger, light truck, heavy truck and bus tires, so as to provide techniques for fabrication of wear surfaces for laboratory tread wear testing that are configured to reproduce a full spectrum of roughness ranges characteristic of actual road surfaces and obtain realistic tread wear test data. In one preferred embodiment, a method of measuring or characterizing tread wear performance of new and/or retreaded tires is provided comprising providing a tire having a tire tread, bringing the tire into contact with a tread wear testing apparatus for testing wear of the tread, the tread wear testing apparatus comprising a road wheel having a substantially rigid hardened wear surface disposed on the road wheel, the wear surface comprising an adhesive mixed with at least one aggregate and configured for hardening and being imprinted with a cast of a road surface on which tread wear of the tire is to be tested, wherein the adhesive is coated onto the road wheel and imprinted with the cast of the road surface when the adhesive is unhardened, the substantially rigid hardened wear surface adapted for emulating one or more surface roughness characteristics of the road surface, applying forces to the tire via the tread wear testing apparatus to simulate a vehicle load, and generating tread wear test data for the tire for analysis.

In another preferred embodiment, a method of fabricating a substantially rigid hardened wear surface for a tire tread wear testing apparatus is provided, the method comprising making a cast of a road surface on which tread wear of the tire is to be tested, providing a layer of adhesive (e.g., heat activated epoxy adhesive) mixed with at least one aggregate and configured for hardening to create the substantially rigid hardened wear surface, and, while the layer of adhesive is still unhardened: (a) coating the layer of adhesive onto a road wheel of the tire tread wear testing apparatus, and (b) stamping an impression of the cast into the layer of adhesive for producing the substantially rigid hardened wear surface adapted for emulating one or more surface roughness characteristics of the road surface.

In another preferred embodiment, a tread wear apparatus is provided for testing tread wear of a tire, comprising a road wheel, a substantially rigid hardened wear surface disposed on the road wheel, the wear surface comprising an adhesive (e.g., heat activated epoxy adhesive) optionally mixed with at least one small aggregate, the adhesive being configured for hardening and being imprinted with a cast of a road surface on which tread wear of the tire is to be tested, wherein the adhesive is coated onto the road wheel and imprinted with the cast of the road surface while the adhesive/aggregate mixture is unhardened, the substantially rigid hardened wear surface adapted for emulating one or more surface roughness characteristics of the road surface, and at least one test wheel configured for having the tire mounted thereon and for being brought into contact with the wear surface of the road wheel for testing the tread wear.

In yet another preferred embodiment, a substantially rigid hardened wear surface is provided for testing tread wear of a tire, the wear surface comprising an adhesive (e.g., heat activated epoxy adhesive) mixed with at least one aggregate and configured for hardening and being imprinted with a cast of a road surface on which tread wear of the tire is to be tested, wherein the adhesive is coated onto a road wheel of a tread wear testing apparatus and imprinted with the cast of the road surface while the adhesive is still unhardened, the substantially rigid hardened wear surface adapted for emulating one or more surface roughness characteristics of the road surface.

BRIEF DESCRIPTION OF THE DRAWINGS

While the appended claims set forth the features of the present invention with particularity, the invention and its advantages are best understood from the following detailed description taken in conjunction with the accompanying drawings, of which:

DETAILED DESCRIPTION OF THE INVENTION

The following examples further illustrate the invention but, of course, should not be construed as in any way limiting its scope.

Figure 1:
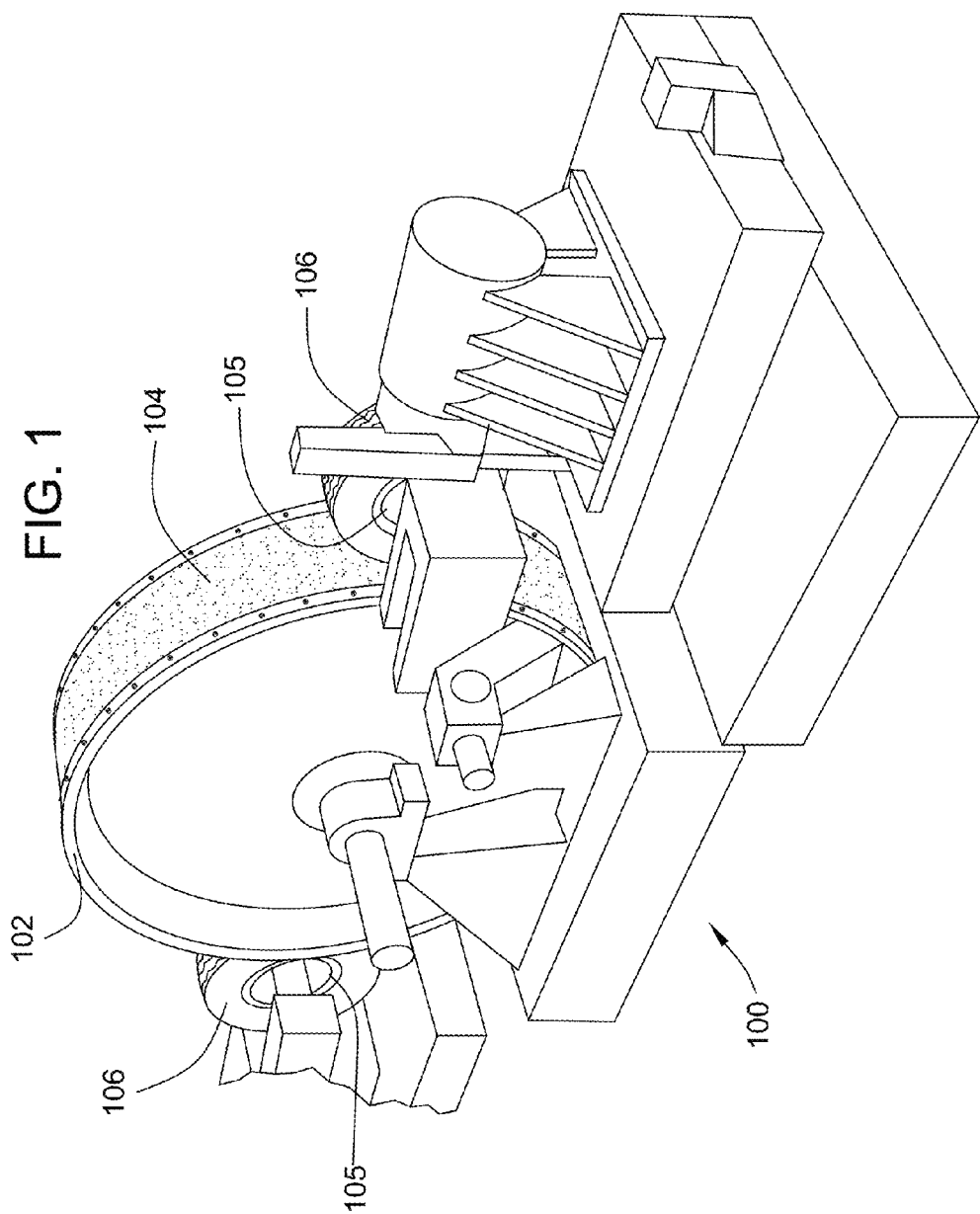
FIG. 1 is a schematic illustrating an apparatus for the design and manufacture of tires, such apparatus including a wear surface for emulating a full spectrum of roughness ranges characteristic of actual road surfaces, as contemplated by a preferred embodiment of the present invention.
Figure 2:
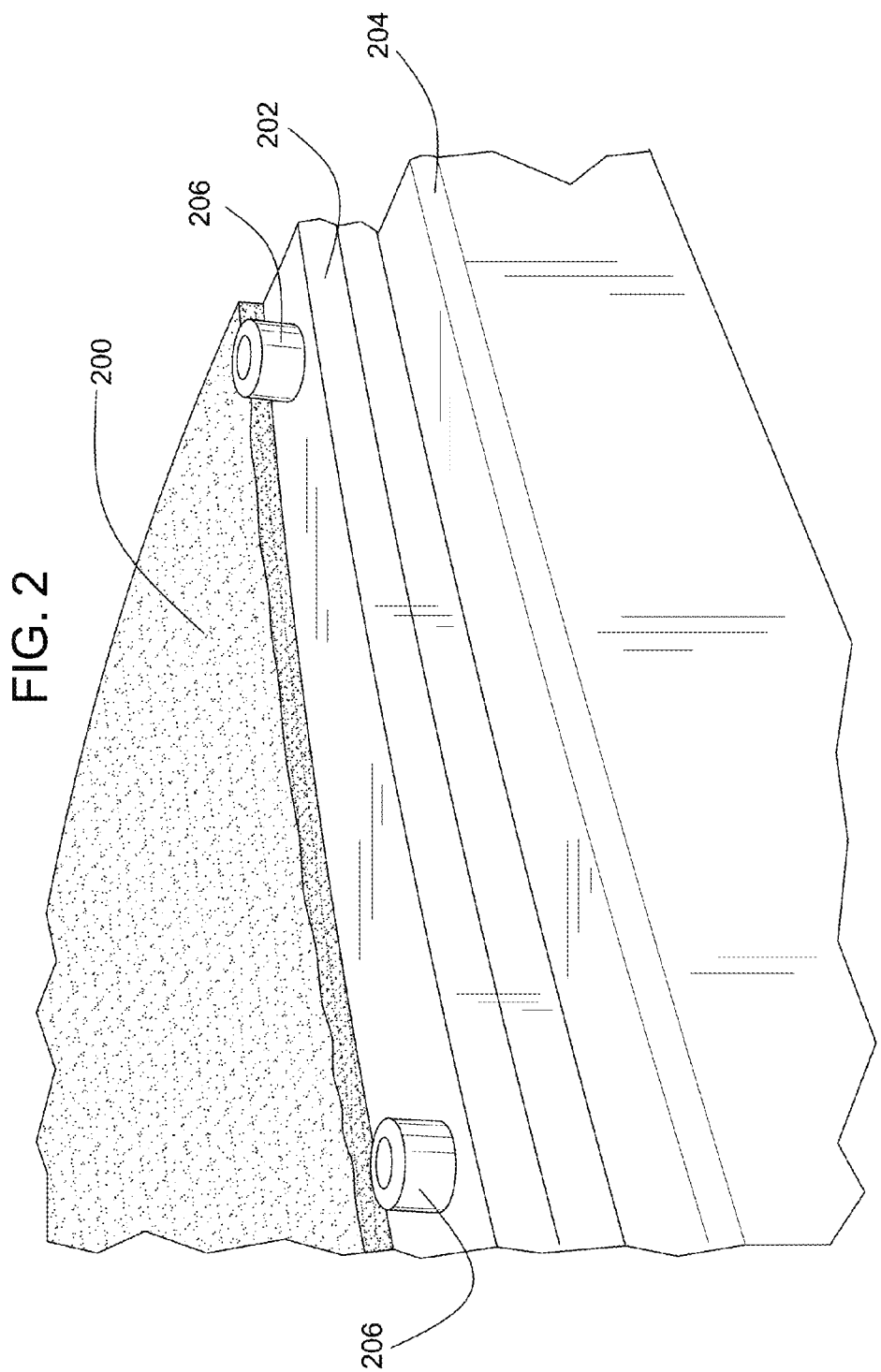
FIG. 2 is a schematic illustrating a cut-out view of a road wheel of the tread wear testing apparatus of FIG. 1 and showing the wear surface disposed on the road wheel, as contemplated by a preferred embodiment of the present invention.

Embodiments of the invention address fabrication of wear surfaces for laboratory tread wear testing that are configured to reproduce a full spectrum of roughness ranges characteristic of actual road surfaces in order to obtain realistic tire wear. With reference to FIG. 1, laboratory tread wear testing is performed via a tread wear machine 100 comprising a road wheel 102 having a substantially rigid hardened wear surface 104. One or more test tires 106, mounted to test wheels 105, are brought into controlled contact with the hardened wear surface 104 for collecting tread wear data under simulated vehicle loads. As shown in FIG. 2, an embodiment of a hardened wear surface 200 is disposed on a steel plate 202 which is fastened to the road wheel 204. The steel plate 202 is rigid and inflexible and is fastened to the road wheel 204 by fasteners 206, such as steel bolts. In an embodiment, the hardened wear surface 200 is disposed on multiple steel plates along the diameter of the road wheel 204. In the illustrated embodiment, the wear surface 200 is coated onto each steel plate 202. As the hardened wear surface 200 itself undergoes wear during the tread wear testing process, staggered replacement of steel plates coated with the wear surface 200 allows for the averaging of surface wear along the circumference of the road wheel 204 and/or may be used for varying the average surface roughness along the road wheel 204. Alternatively, when steel plates are not used, the wear surface 200 is coated directly onto the surface of the road wheel 204. As discussed in further detail below, the substantially rigid hardened wear surface 200 is configured to emulate the surface roughness characteristics of an actual road surface for obtaining laboratory tread wear data comparable to actual outdoor road surface testing. Advantageously, the wear surface 200 also provides an extended service life. The service life of the hardened wear surface 200 in accordance with an embodiment of the present invention exceeds five hundred thousand (500,000) miles, which is approximately a ten-fold increase over existing wear surfaces, including sand paper-based wear surfaces.

For purposes of the following discussion, surface roughness approximately in the 0.1-1.0 mm range is referred to as a "macro" roughness and surface roughness above approximately 1 mm, for example in the range from approximately above 1 mm and up to at least 200 mm, and including the range of approximately above 1.0 mm and up to approximately 10 mm referenced in the following embodiments, is referred to as "large-macro" roughness. Emulation of road surfaces that include a large-macro roughness is desirable in order to reproduce the proper contact area between a tire and a surface, which, in turn, affects the contact stresses and local slippage within a contact region.

Surface Roughness Measurement Techniques

Figure 3:
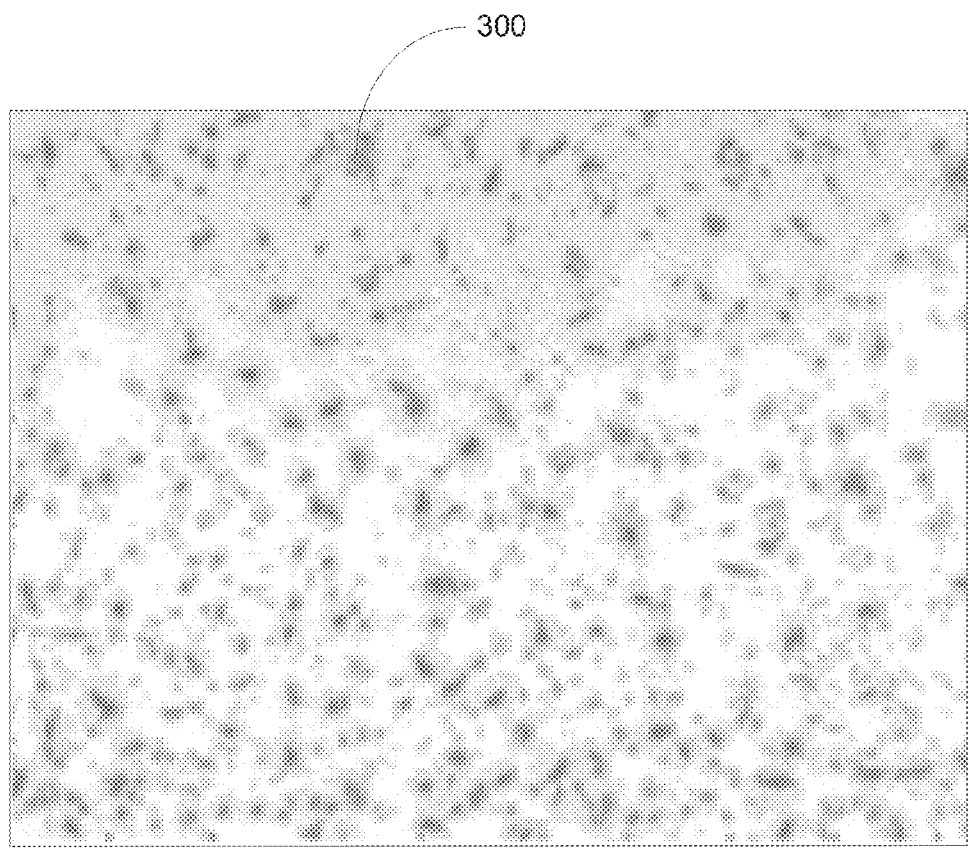
FIG. 3 is a schematic illustrating pressure-sensitive paper showing areas of contact between a tire and a road surface, as contemplated by a preferred embodiment of the present invention.
Figure 4:
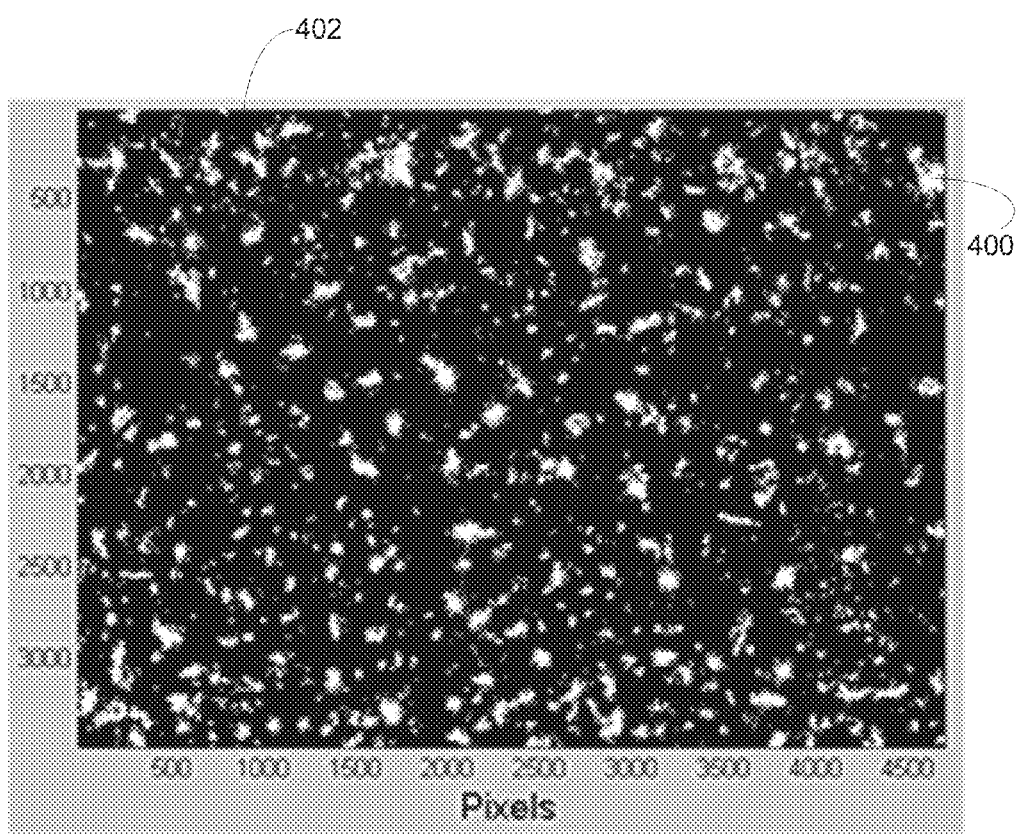
FIG. 4 is a schematic illustrating an example of computer implemented analysis that determines the presence of contact and non-contact junctions based on a sensitivity threshold of the pressure-sensitive paper of FIG. 3, as contemplated by a preferred embodiment of the present invention.

Actual road surfaces, such as pavements, can be quite varied and include different degrees of both macro and large-macro roughness components. The large-macro roughness particularly affects the contact area between the tire and the pavement. This can be visualized and quantified using pressure sensitive paper. With reference to FIG. 3, when a smooth tread control tire is slowly rolled over a piece of pressure sensitive paper, the dark areas 300 in the resulting imprint represent areas of contact or junction between the tire and a road surface, such as a pavement. One way to quantify differences in the large-macro roughness of a pavement is via a computer implemented analysis of the distribution of the size of these individual contact junctions. To this end, an image of the pressure sensitive paper is digitized. Next, computer implemented pixel-by-pixel analysis is performed to determine the presence of contact and non-contact junctions based on the lowest possible sensitivity threshold of the paper. FIG.

Figure 5:
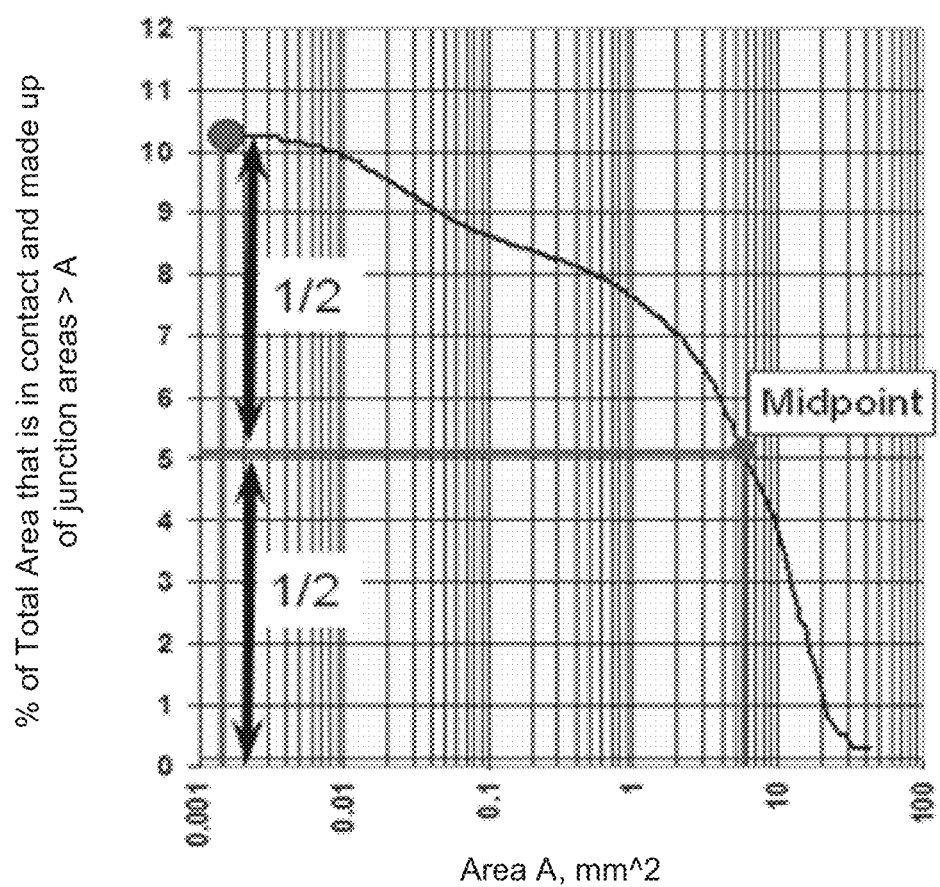
FIG. 5 is a diagram illustrating the distribution of the areas of contact junctions, as contemplated by a preferred embodiment of the present invention.

4 shows the result of the determination, where all contact junctions 400 are shown in the light areas and all non-contact junctions 402 are shown in the dark areas. The last step is to calculate a distribution of the areas of the contact junctions. In this example, which represents a worn hot-mixed asphalt pavement, there are 39,809 junctions ranging in size from 0.0018 mm$^2$ (1 square pixel) to over 30 mm$^2$, as illustrated by the x-axis of FIG. 5. The total contact area is 10.3% of the area analyzed (y-axis). A useful metric that most highly discriminates between different pavements is the midpoint area. The midpoint area corresponds to 50% of the total contact area. In this example, the midpoint area is 5.81 mm$^2$.

Figure 6:
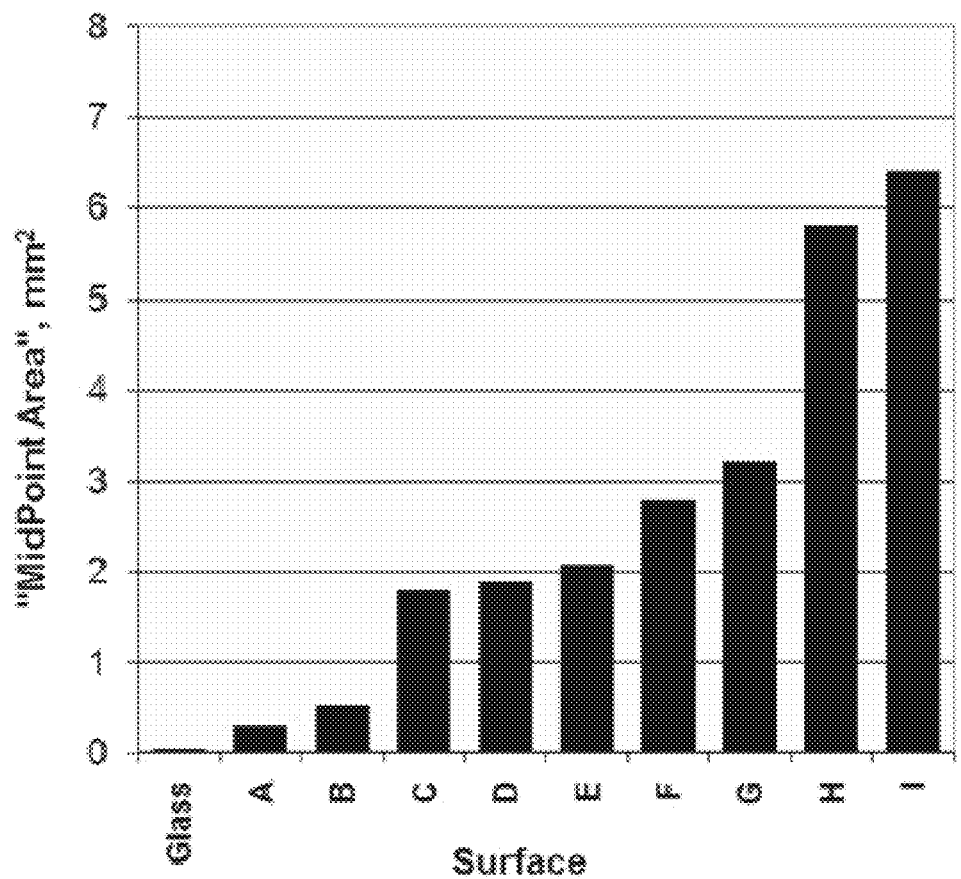
FIG. 6 is a diagram illustrating midpoint area values for a variety of hot mixed asphalt and chip/seal pavements, as contemplated by a preferred embodiment of the present invention.

The midpoint area metric is dependent on the tire tread pattern, tread compound stiffness, and load but if these factors are held fixed, then it offers a meaningful way to compare the large-macro roughness from one pavement to another. FIG. 6 shows midpoint area values for a variety of hot mixed asphalt and chip/seal pavements, as well as a glass plate used as a reference to illustrate a surface with no measurable roughness.

Figure 7A:
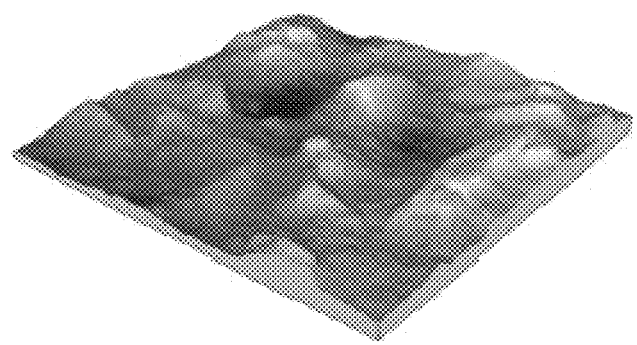
FIGS. 7a-7d are diagrams illustrating three-dimensional laser scans of common pavement types, as contemplated by a preferred embodiment of the present invention.
Figure 7B:
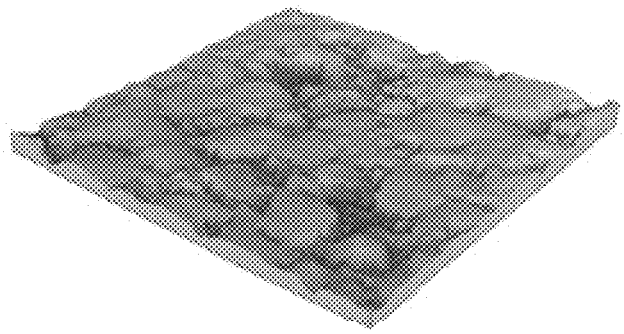
Figure 7C:
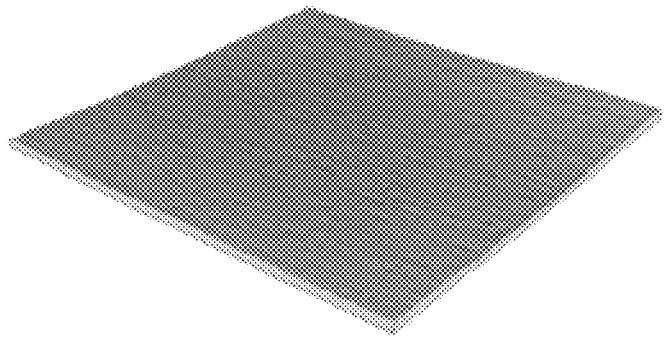
Figure 7D:
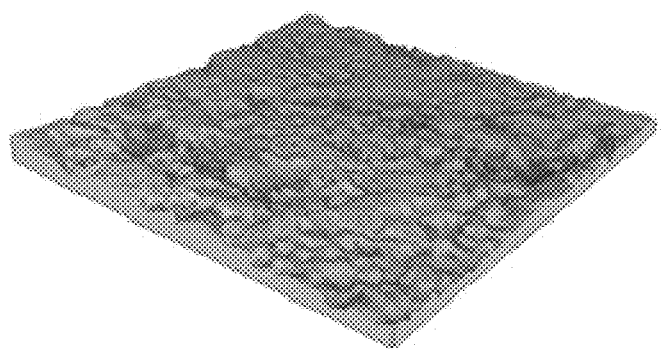

An alternative method for measuring surface roughness involves scanning the surface with a precision laser mounted on an x-y slider table. In one embodiment, height measurements are made at 0.004 mm spacing along a minimum of 50 mm long lines spaced 5 mm apart. The output of the scanner is stored in a computer readable medium as an x-y-z data file that preferably includes a minimum of 120,000 data points. FIGS. 7a-7d are three-dimensional plots of laser scans of some common pavement types. In this example, each scan includes 156,000 evenly spaced points. These figures show different levels of large-macro and macro roughness present in a particular surface. Specifically, FIG. 7a shows a digital scan of a rural road having a high level of large-macro and a low level of macro roughness components. FIG. 7b shows a digital scan of an asphalt pavement having an intermediate level of large-macro roughness and a low level of macro roughness components. FIG. 7c shows a digital scan of a smooth concrete pavement showing low levels of both large-macro and macro roughness components. Finally, FIG. 7d illustrates a digital scan of a city road pavement having a low level of large-macro roughness and an intermediate level of macro roughness component. To facilitate the comparison of the macro roughness levels, these three-dimensional plots have a magnified height or z-axis.

Figure 8:
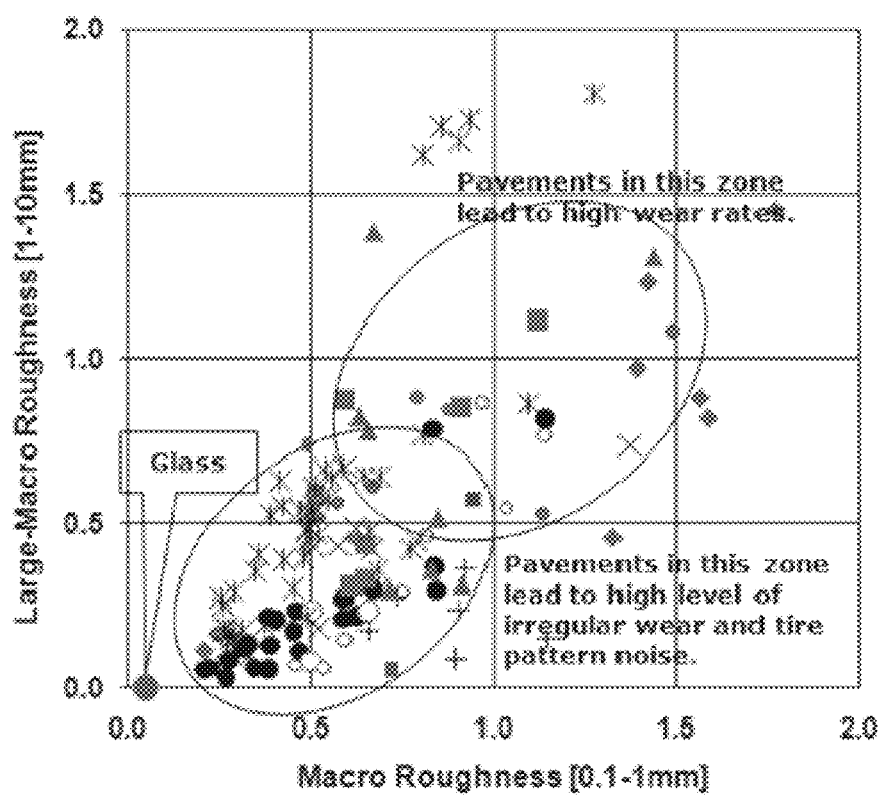
FIG. 8 is a diagram illustrating large-macro and macro surface roughness values determined from computer implemented fractal/wavelength analysis of pavements in areas across North and Latin America, as contemplated by a preferred embodiment of the present invention.

Suitable examples of computer analysis methods for extracting roughness parameters from digital data sets include techniques that employ ISO metrics, spectrum analysis and fractal methods. FIG. 8 shows large-macro and macro surface roughness values determined from computer implemented fractal/wavelength analysis of over one hundred and fifty (150) pavements taken in areas across North and Latin America. Different areas are depicted by different symbols. The units on these axes refer to the rate of change of the total profile length with respect to the log of the measurement segment length. In other words, if the value is high in the large-macro range, then the surface has high levels of amplitude in the 1.0-10.0 mm range of wavelengths.

As seen from the foregoing discussion, there is a wide range of pavements and corresponding surface roughness distributions that need to be considered when developing abrasive wear surfaces for indoor tread wear testing. The large-macro characteristics of the pavement particularly affect the contact between the tire and pavement. The above metrics are used to compare and design indoor wear surfaces to mimic specific types of pavements in accordance with the embodiments of wear surface fabrication techniques described below.

Wear Surface Fabrication

Figure 9:
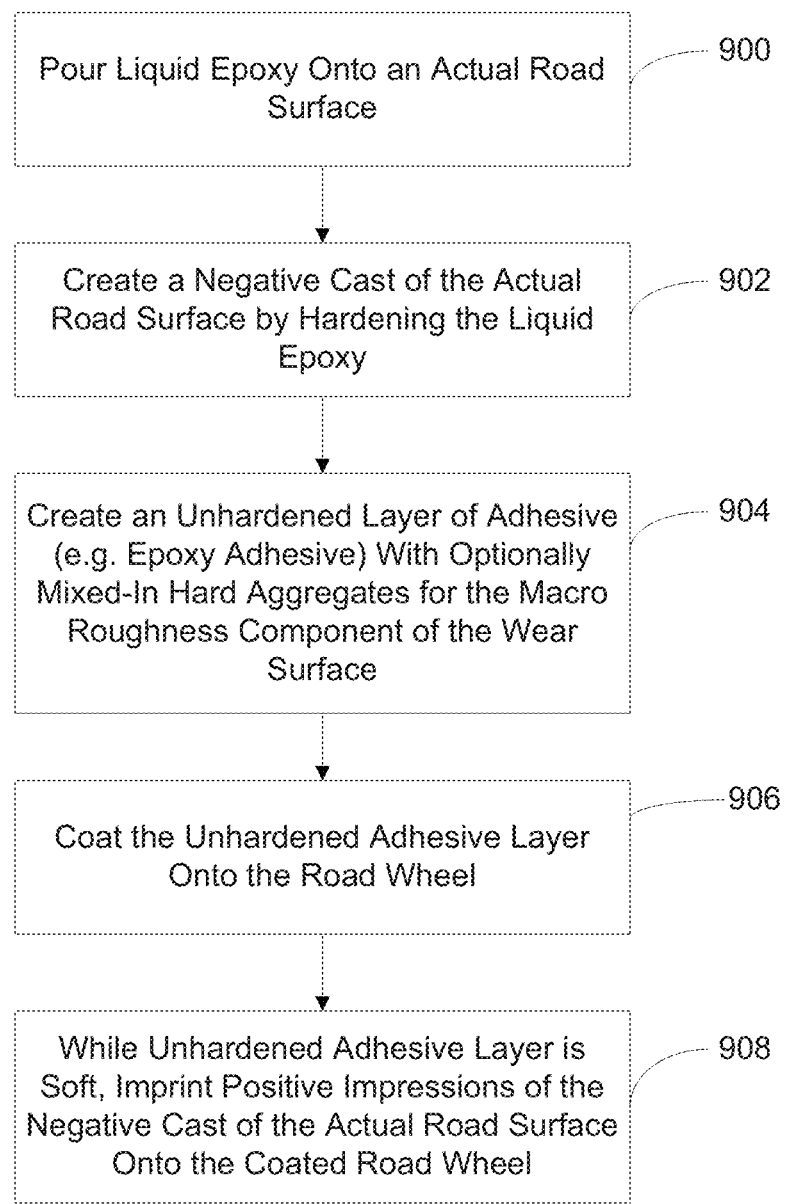
FIG. 9 is a diagram illustrating a process for manufacturing a hardened wear surface, as contemplated by a preferred embodiment of the present invention.

Turning to FIG. 9, an embodiment of a process for manufacturing a wear surface 200 is shown. In this embodiment, a "negative" cast of an actual road surface is made and then used to stamp a "positive" impression into a layer of epoxy adhesive which is not yet fully hardened. Specifically, in step 900, a casting substance, such as liquid epoxy having a short cure time (e.g., approximately five minutes), is poured onto an actual road surface, for example onto a sample of actual pavement. In step 902, a negative cast capturing at least the large-macro roughness component of the actual road surface is made by hardening the liquid epoxy. In one embodiment, the cast size is approximately 10 by 10 cm.

Next, a surface for covering the road wheel is created. The adhesive, such as a heat activated epoxy adhesive, is first softened by heating it on a hot plate, for example to approximately 55° C. To represent the macro roughness spectrum of the road surface, hard aggregates are mixed into the unhardened/softened layer of adhesive, step 904. Examples of hard aggregates mixed into a layer of epoxy adhesive to produce the desired roughness component in the approximately 0.1-1.0 mm macro range include silica or quartz, for example as described in the commonly owned Japanese Patent No. JP 3234678 (B2), which is incorporated herein by reference in its entirety for all that it teaches. Further embodiments of hard aggregates include granite, basalt or similar mineral with sufficiently high hardness. In an embodiment, the hard aggregates range between 0.1-3 mm in diameter and are of predetermined hardness (e.g., Mohs hardness >4) so as to further extend the durability of the wear surface. The still unhardened/soft layer of adhesive with mixed-in hard aggregates is then coated onto the road wheel 204, preferably within approximately fifteen to twenty minutes after being heated, step 906. In embodiments, the unhardened layer of adhesive is coated either onto metal plates fastened to the road wheel 204 or directly to the surface of the road wheel 204 when the metal plates are not employed. While the coated epoxy adhesive is still soft, such as within approximately five minutes, a positive impression of the actual road surface is imprinted using the negative cast in order to emulate the large-macro roughness component of the surface roughness of an actual road surface (preferably, approximately in the range of above 1 mm to 10 mm), step 908. The resulting imprinted surface is preferably cured, for example overnight, prior to use. In an alternative embodiment, the negative cast of the actual road surface is used to emulate both macro and large-macro levels of surface roughness. Upon hardening, the layer of epoxy adhesive coated onto the road wheel 204 or steel plates 202 and imprinted with an impression of the actual road surface produces a substantially rigid hardened wear surface 200 suitable for tread wear testing. In addition to improved road surface roughness emulation, the hardened wear surface 200 produced in accordance with the embodiments of the present invention provides an increased service life which is an order of magnitude greater than that of the existing wear surfaces, (e.g., at least 500,000 mile service life is achieved as compared to approximately 50,000 mile average service life for sand paper-based wear surfaces, for instance).

Figure 10:
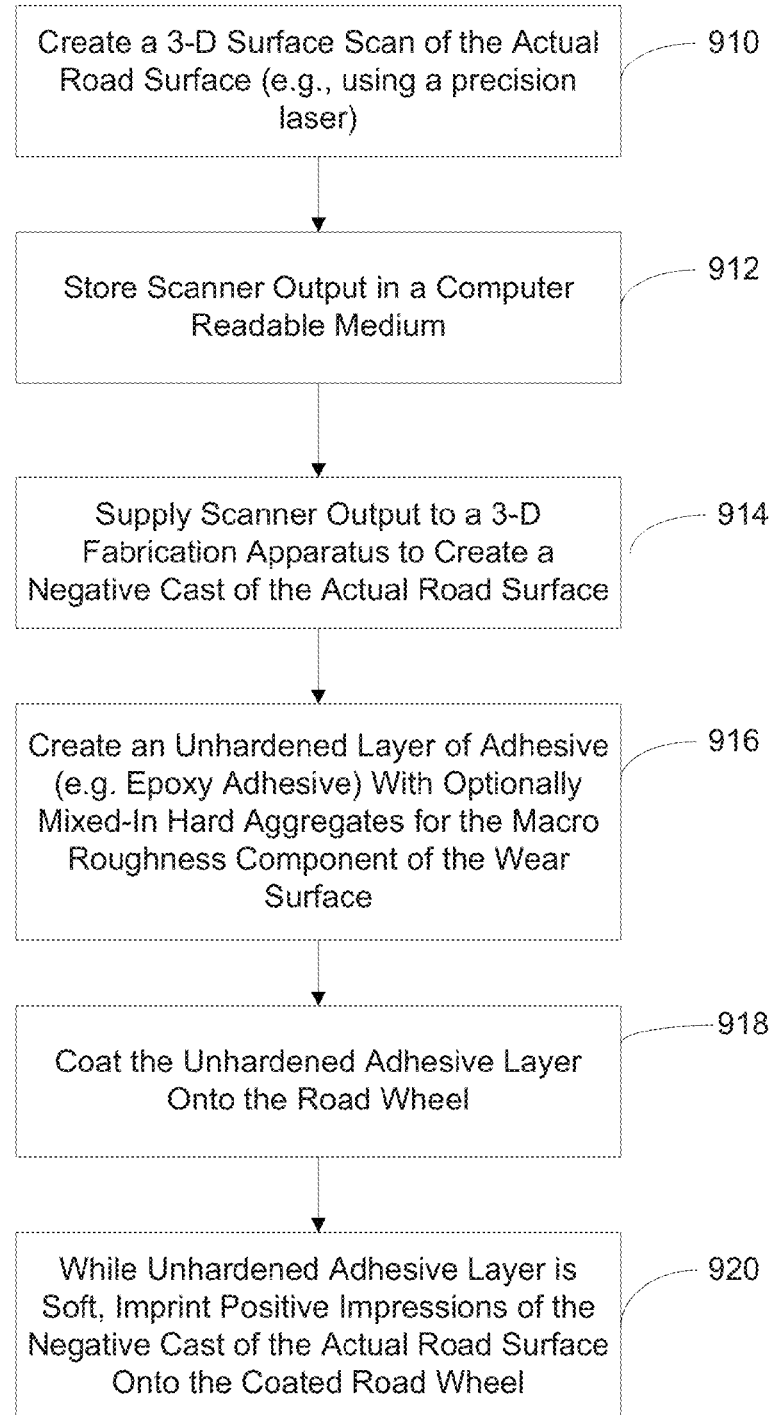
FIG. 10 is a diagram illustrating a process for manufacturing a hardened wear surface, as contemplated by another preferred embodiment of the present invention.

In another embodiment, the negative cast is created through a three-dimensional machining process driven by the digital files created from laser scanning of the actual road surface. Turning to FIG. 10, an embodiment of a process for creating a wear surface by way of three-dimensional machining is shown. In step 910, an actual road surface (or a sample thereof) is scanned with a precision laser that is mounted on an x-y table. In an embodiment, spacing of the laser scanned data is equal in both x and y directions, while the height measurements are made at a relatively fine scale. In step 912, the laser scanner output is stored in a non-transitory computer readable medium, such as a hard drive, optical disk, flash memory, RAM/ROM memory, or the like. The laser scanner output comprises a 3-D x-y-z data file representing surface roughness readings obtained from the surface scan (see FIGS. 7a-7d). In an embodiment, the laser scanner preferably takes approximately 250,000 surface readings to create a data file with the corresponding number of data points. In step 914, a three-dimensional (3-D) fabrication machine having a programmable input (e.g., by way of a Programmable Logic Controller) reads the digital scan file from the computer readable medium to fabricate, via computer executable instruction control, a negative cast of the actual road surface having at least a large-macro roughness component. As discussed in connection with FIG. 9 above, while the adhesive coated onto the road wheel 204 is still soft, a positive impression of the actual road surface is imprinted using the 3-D fabricated negative cast in order to emulate the large-macro roughness component of the actual road surface, steps 916-920. In embodiments, the three-dimensional fabrication of the negative cast of the actual road surface comprises three-dimensional machining, stereo lithography, three-dimensional milling, three-dimensional molding, or similar three-dimensional fabrication techniques.

In another embodiment, a negative cast is created via a high resolution silicon molding compound that is pressed onto a pavement road surface. The high resolution silicon molding compound is capable of capturing a wide spectrum of surface roughness detail. The molding compound is removed from the pavement within a short time period, such as within a minute. After the negative cast has thoroughly cured, it is then used to make an intermediate positive cast also using a silicon molding compound as the casting substance. The positive silicon cast, in turn, is used to create a final negative cast made of aluminum for imprinting onto the yet unhardened layer of adhesive coated onto the road wheel, as described above. Advantageously, the aluminum negative cast created in accordance with the foregoing embodiment includes high resolution surface roughness detail and provides an extended service life.

Figure 11:
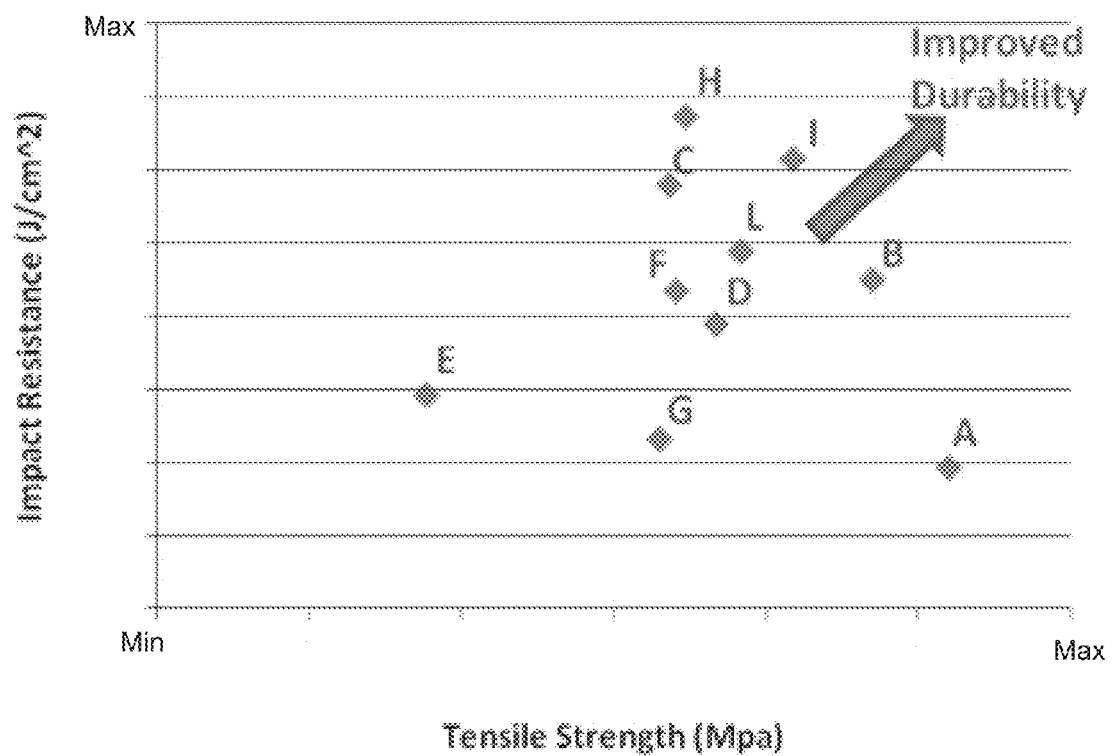
FIG. 11 is a diagram illustrating selection criteria for a substantially rigid hardened wear surface, as contemplated by a preferred embodiment of the present invention.

Turning to FIG. 11, a heat activated epoxy adhesive for coating onto the road wheel is selected for it strength, rigidity, and bonding strength when it is hardened. In an embodiment, epoxy tensile strength, compressive strength, and shear strength parameters are used as epoxy selection criteria. Similarly, the mixture of epoxy and hard aggregate(s) is also optimized for improved durability by maximizing tensile strength and impact resistance of the adhesive layer with mixed-in hard aggregate(s). As shown in FIG. 11, various samples (A through L) having different epoxy-to-aggregate weight ratios are tested for tensile strength and Charpy impact resistance so as to select the samples that produce high values of both tensile strength and impact resistance.

Figure 12:
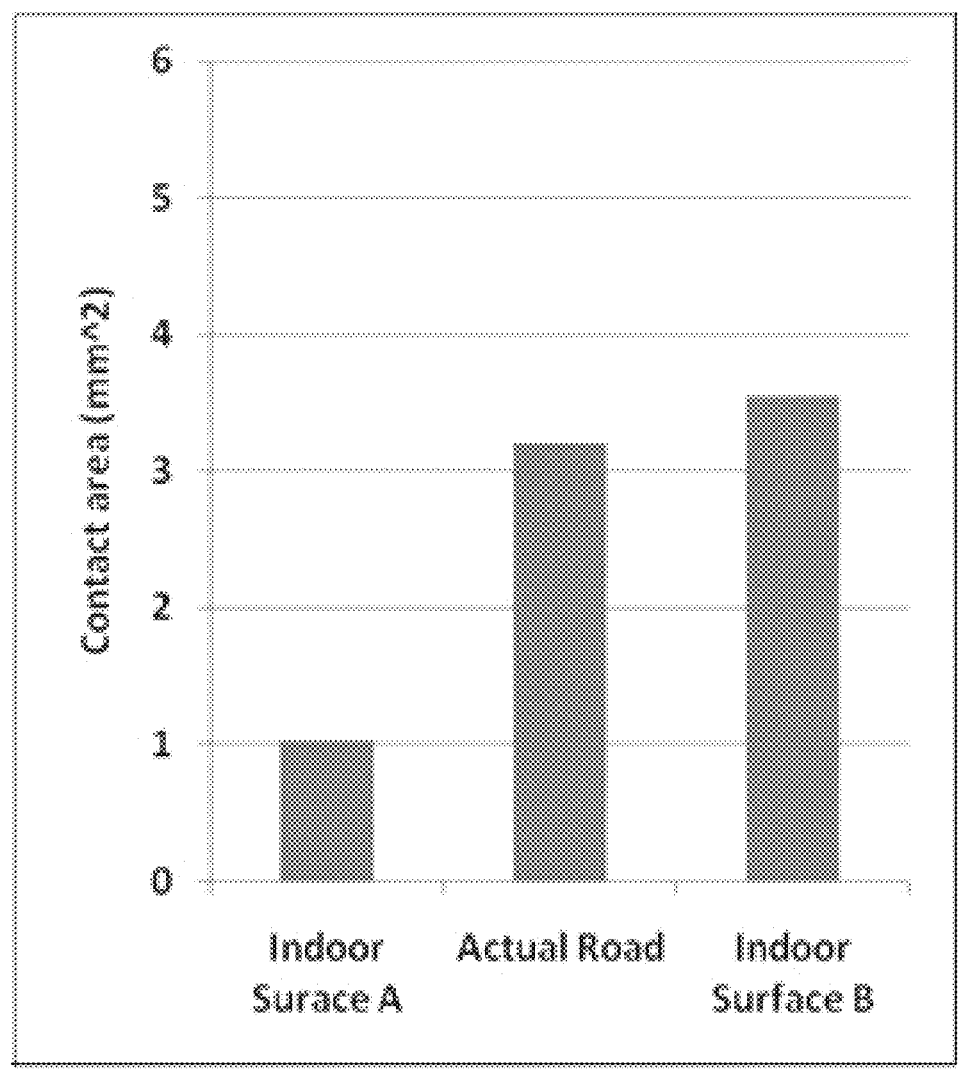
FIG. 12 is a diagram illustrating the contact area metric for an actual road surface and indoor wear surfaces before and after large-macro roughness imprinting, as contemplated by a preferred embodiment of the present invention.

An asphalt road pavement was used to construct a negative cast and then imprint into an indoor surface. FIG. 12 shows the contact area metric for an actual road surface, as well as two indoor wear surfaces before and after large-macro roughness imprinting (shown as Indoor Surface A and Indoor Surface B, respectively). The midpoint contact area metric for the indoor wear surfaces increased from 1.0 mm$^2$ (before imprinting) to 3.6 mm$^2$ (after imprinting), which closely followed the midpoint metric of the actual road surface that measured at 3.4 mm$^2$.

Figure 13:
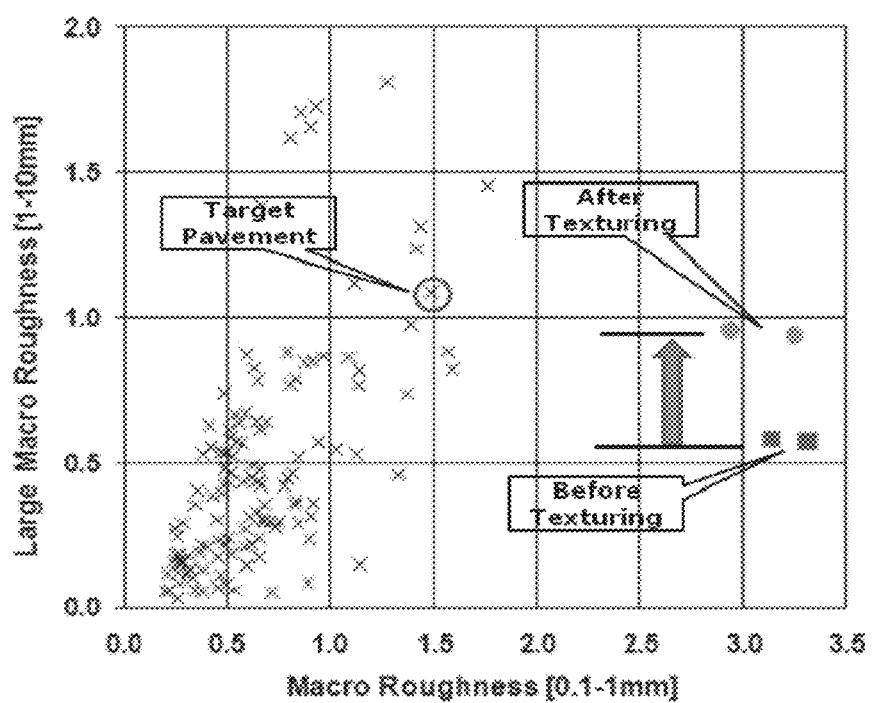
FIG. 13 is a diagram illustrating roughness metrics for the road surface and the two wear surfaces of FIG. 12, as contemplated by a preferred embodiment of the present invention.

As shown in FIG. 13, roughness metrics were also calculated for the actual pavement road surface and the two indoor wear surfaces. The large-macro duplication process increased the large-macro roughness metric by 65%, from the 0.57-0.58 level to 0.94-0.96 level. The actual pavement that was duplicated had a large-macro level of 1.09. Therefore, it is quite evident that the foregoing large-macro emulation process introduces a much more realistic level of large-macro roughness to engineered wear surfaces for indoor laboratory tread wear testing.

Effects of the Large-Macro Roughness on Tire Wear

Figure 14:
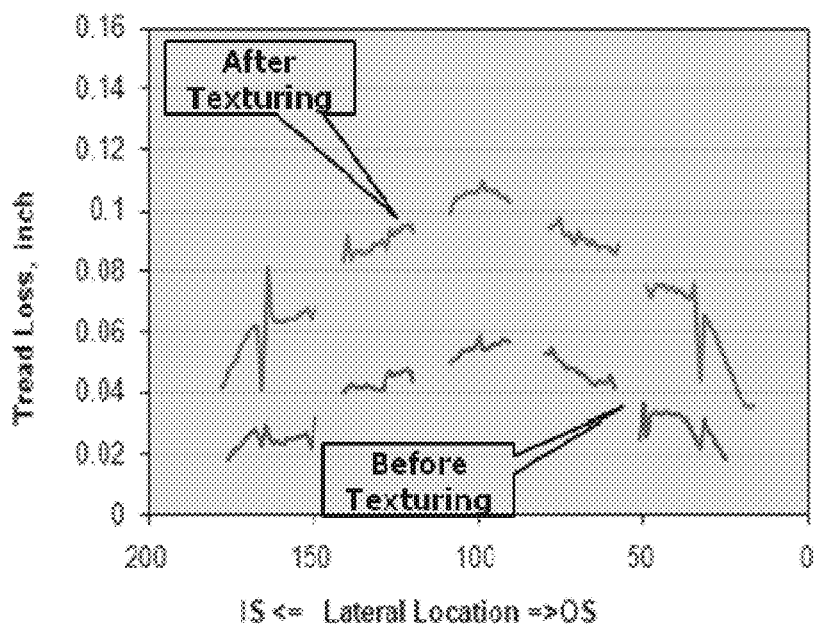
FIGS. 14-15 are diagrams illustrating tread wear parameters before and after large macro roughness texturing of the wear surface, as contemplated by a preferred embodiment of the present invention.
Figure 15:
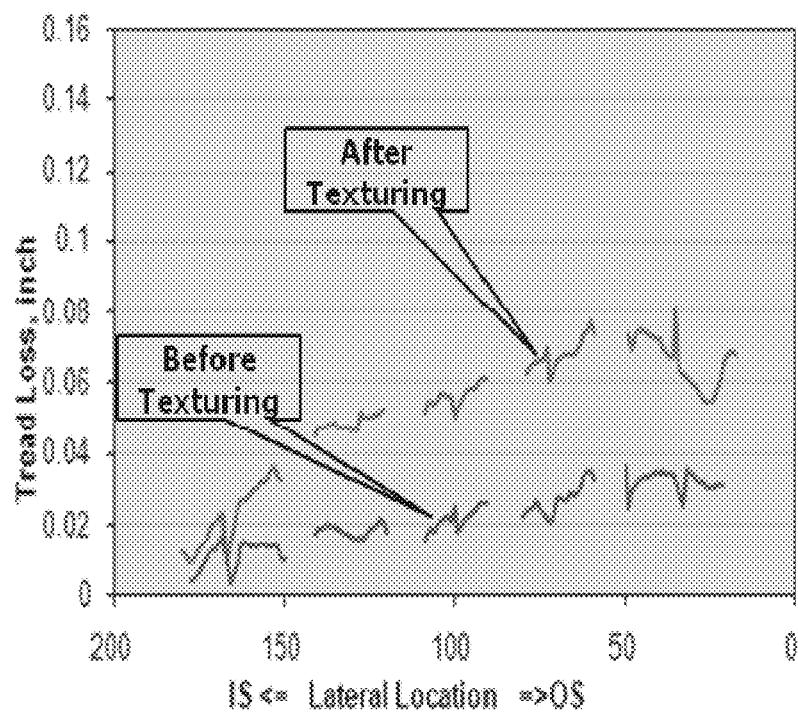

Results from two different indoor wear tests conducted on both Indoor wear Surface A (before imprinting) and Indoor wear Surface B (after imprinting) are shown in FIGS. 14-15. The first test used test loads typical of the front position of a front wheel drive vehicle, which typically lead to center wear. Surface B produced about 2.2 times faster wear and a slightly higher level of center wear than surface A. The second test used test loads typical of the front position of a rear wheel drive vehicle with a large toe in force which lead to outside shoulder (OS) wear. Surface B produced 1.7 times faster wear and slightly higher level of shoulder wear than Surface A.

Figure 16:
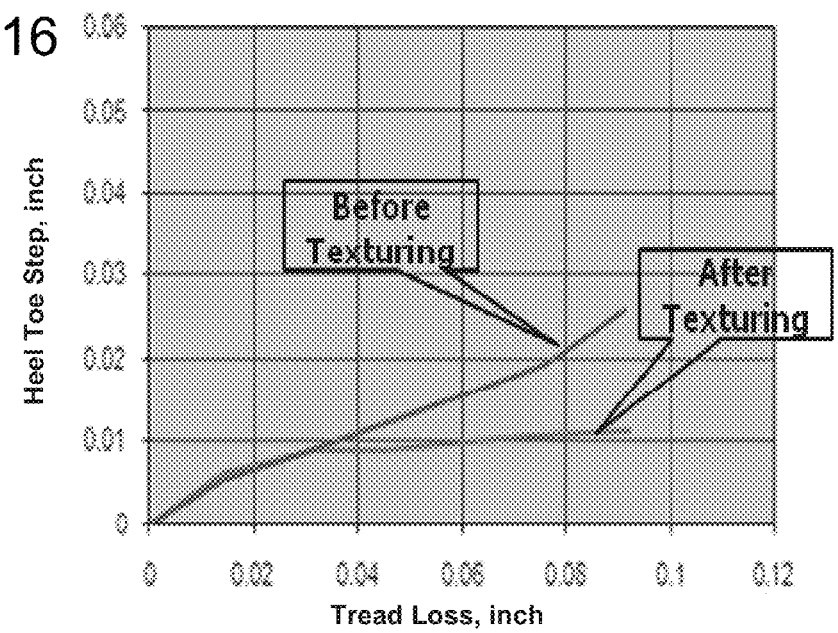
FIGS. 16-17 are diagrams illustrating additional tread wear parameters before and after large macro roughness imprinting, in accordance with a preferred embodiment of the invention.
Figure 17:
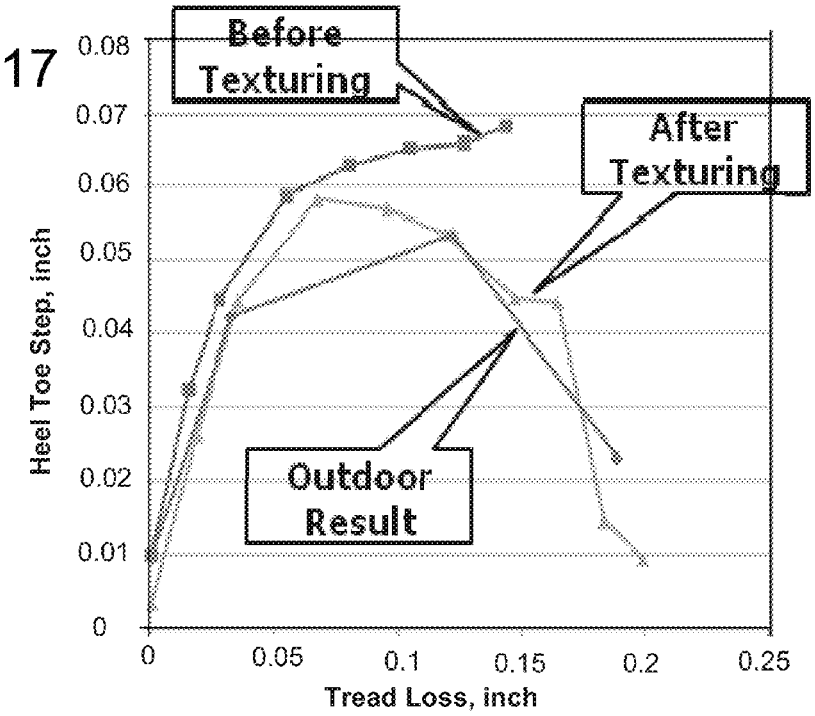

A type of irregular wear called heel/toe results from circumferentially uneven wear on individual tread elements or tread lugs. This creates a step wear across the shoulder slots between the front edge of one tread lug and the back edge of the adjacent tread lug. This type of irregular wear often increases rapidly as the tire begins to wear in actual service but then levels off or even starts to decrease slightly as the tire continues to wear. As shown in FIG. 16, the introduction of the large-macro roughness produces some tendencies with respect to this type of irregular wear which are more typical of in-service conditions. FIG. 17 shows the results from a second series of indoor wear tests compared with actual outdoor results.

In the foregoing discussion, embodiments of a process have been demonstrated that permits duplication of surface roughness from an actual road pavement in the large macro amplitude range (e.g., including in the surface roughness range of approximately above 1 mm to approximately 10 mm) for the purpose of fabricating a realistic wear surface for laboratory tire tread wear testing machines that generate data which facilitates research and development, as well as design and manufacturing of new and retreaded tires. The generated tread wear test data is analyzed to compare tread wear characteristics of various tread compounds and tread patterns, as well as to quantify a particular tire with a given tread composition and pattern into a corresponding tread wear category (e.g., based on a predetermined tread wear classification scale, such as "100," "200", "300," etc wear rate where higher numbers indicate longer expected tread life). Also, in the tire manufacturing context, the generated tread wear test data may be used to compare the manufactured tire against the predetermined tread wear classification.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of fabricating a substantially rigid hardened wear surface for a tire tread wear testing apparatus, the method comprising:
    making a negative cast of a road surface on which tread wear of the tire is to be tested;
    providing a layer of adhesive mixed with at least one aggregate and configured for hardening to create the substantially rigid hardened wear surface;
    while the layer of adhesive is unhardened:
    (a) coating the layer of adhesive onto a road wheel of the tire tread wear testing apparatus; and
    (b) stamping an impression of the negative cast to create a positive impression of the road surface into the layer of adhesive for producing the wear surface;
    wherein the wear surface is configured to capture a large-macro roughness of the road surface such that a contact area affecting contact stresses and local slippage within a contact region between the tire and the wear surface substantially reproduces one or more surface roughness characteristics of the road surface.

2. The method of claim 1 wherein the one or more surface roughness characteristics comprise a macro roughness of the road surface.

3. The method of claim 1 wherein the at least one aggregate is a hard aggregate.

4. The method of claim 3 wherein the hard aggregate is selected from the group consisting of silica, quartz, granite, and basalt.

5. The method of claim 1 wherein the layer of adhesive comprises epoxy adhesive coated onto one or more metal plates fastened to the road wheel.

6. The method of claim 1 wherein the layer of adhesive comprises epoxy adhesive coated directly to a surface of the road wheel.

7. The method of claim 1 further comprising making the cast by applying a casting substance onto the road surface and hardening the casting substance.

8. The method of claim 7 wherein the casting substance is selected from the group consisting of liquid epoxy and silicon molding.

9. The method of claim 1 wherein making the cast further comprises:
    creating a three-dimensional scan of the road surface;
    storing the three-dimensional scan in a computer readable medium; and
    performing three-dimensional fabrication of the cast based on the road surface scan.

10. A tread wear apparatus for testing tread wear of a tire, comprising:
    a road wheel;
    a substantially rigid hardened wear surface disposed on the road wheel, the wear surface comprising an adhesive mixed with at least one aggregate and configured for hardening and being imprinted with a negative cast of a road surface on which tread wear of the tire is to be tested, wherein the adhesive is coated onto the road wheel and a positive impression of the road surface is imprinted into a layer of the adhesive with the negative cast of the road surface when the adhesive is unhardened,
    wherein the substantially rigid hardened wear surface is configured to capture a large-macro roughness of the road surface such that a contact area affecting contact stresses and local slippage within a contact region between the tire and the substantially rigid hardened wear surface substantially reproduces one or more surface roughness characteristics of the road surface; and
    at least one test wheel configured for having the tire mounted thereon and for being brought into contact with the wear surface of the road wheel for testing the tread wear.

11. The tread wear apparatus of claim 10 wherein the one or more surface roughness characteristics comprise a macro roughness of the road surface.

12. The tread wear apparatus of claim 10 wherein the at least one aggregate is a hard aggregate.

13. The tread wear apparatus of claim 12 wherein the hard aggregate is selected from the group consisting of silica, quartz, granite, and basalt.

14. The tread wear apparatus of claim 10 wherein the adhesive comprises epoxy adhesive coated onto one or more metal plates fastened to the road wheel.

15. The tread wear apparatus of claim 10 wherein the adhesive comprises epoxy adhesive coated directly to a surface of the road wheel.

16. The tread wear apparatus of claim 10 wherein the cast is made by applying a casting substance onto the road surface and hardening the casting substance.

17. The tread wear apparatus of claim 16 wherein the casting substance is selected from the group consisting of liquid epoxy and silicon molding.

18. The tread wear apparatus of claim 10 wherein the cast is made by three-dimensional fabrication based on a three-dimensional scan of the road surface.

19. A substantially rigid hardened wear surface for testing tread wear of a tire, the substantially rigid hardened wear surface comprising an adhesive mixed with at least one aggregate and configured for being hardened and imprinted with a negative cast of a road surface on which tread wear of the tire is to be tested, wherein the adhesive is coated onto a road wheel of a tread wear testing apparatus and a positive impression of the road surface is imprinted into a layer of the adhesive with the negative cast of the road surface when the adhesive is unhardened, and wherein the wear surface is configured to capture a large-macro roughness of the road surface such that a contact area affecting contact stresses and local slippage within a contact region between the tire and the wear surface substantially reproduces one or more surface roughness characteristics of the road surface.

20. The wear surface of claim 19 wherein the one or more surface roughness characteristics comprise a macro roughness of the road surface.

21. The wear surface of claim 19 wherein the at least one aggregate is a hard aggregate.

22. The wear surface of claim 21 wherein the hard aggregate is selected from the group consisting of silica, quartz, granite, and basalt.

23. The wear surface of claim 19 wherein the adhesive comprises epoxy adhesive coated onto one or more metal plates fastened to the road wheel.

24. The wear surface of claim 19 wherein the adhesive comprises epoxy adhesive coated directly to a surface of the road wheel.

25. The wear surface of claim 19 wherein the cast is made by applying a casting substance onto the road surface and hardening the casting substance.

26. The wear surface of claim 25 wherein the casting substance is selected from the group consisting of liquid epoxy and silicon molding.

27. The wear surface of claim 19 wherein the cast is made by three-dimensional fabrication based on a three-dimensional scan of the road surface.

28. A method of analyzing tread wear of a tire comprising:
bringing a tire having a tread into contact with a tread wear testing apparatus for testing wear of the tread, the tread wear testing apparatus comprising a road wheel having a substantially rigid hardened wear surface disposed on the road wheel,
wherein the wear surface comprises an adhesive mixed with at least one aggregate and configured for hardening and being imprinted with a negative cast of a road surface on which tread wear of the tire is to be tested,
wherein the adhesive is coated onto the road wheel and a positive impression of the road surface is imprinted into a layer of the adhesive with the negative cast of the road surface when the adhesive is unhardened, and
wherein the substantially rigid hardened wear surface is configured to capture a large-macro roughness of the road surface such that a contact area affecting contact stresses and local slippage within a contact region between the tire and the wear surface substantially reproduces one or more surface roughness characteristics of the road surface;
applying forces to the tire via the tread wear testing apparatus to simulate a vehicle load; and
generating tread wear test data for the tire for analyzing the tread wear.

29. The method of claim 28 wherein the tire is a new tire.

30. The method of claim 28 wherein the tire includes a retreaded tread pattern.

31. The method of claim 28 wherein the one or more surface roughness characteristics comprise a macro roughness of the road surface.

32. The method of claim 28 wherein the at least one aggregate is a hard aggregate.

33. The method of claim 28 wherein the adhesive comprises epoxy adhesive coated onto one or more metal plates fastened to the road wheel.

34. The method of claim 28 wherein the adhesive comprises epoxy adhesive coated directly to a surface of the road wheel.

35. The method of claim 28 wherein the cast is made by applying a casting substance onto the road surface and hardening the casting substance.

36. The method of claim 35 wherein the casting substance is selected from the group consisting of liquid epoxy and silicon molding.

37. The method of claim 28 wherein the cast is made by three-dimensional fabrication based on a three-dimensional scan of the road surface.

* * * * *